United States Patent [19]

Milstein et al.

[11] Patent Number: 4,472,500
[45] Date of Patent: Sep. 18, 1984

[54] RAT MYELOMA CELL LINES

[75] Inventors: Cesar Milstein, Cambridge; Bruce W. Wright, Comberton, both of England

[73] Assignee: National Research Development Corporation, London, England

[21] Appl. No.: 281,038

[22] Filed: Jul. 7, 1981

[30] Foreign Application Priority Data

Jul. 7, 1980 [GB] United Kingdom ............... 8022206

[51] Int. Cl.$^3$ .................. A61K 39/00; C12P 21/00; C12N 15/00; C12N 5/00; C12R 1/91
[52] U.S. Cl. ................................ 435/68; 424/85; 435/172.2; 435/240; 435/948; 935/103; 935/105
[58] Field of Search ............... 424/85; 435/68, 240, 435/241, 172

[56] References Cited

U.S. PATENT DOCUMENTS

4,350,683  9/1982  Galfre et al. .................. 435/240

FOREIGN PATENT DOCUMENTS

2039948  8/1980  United Kingdom ............... 424/86

OTHER PUBLICATIONS

Kearney et al; J. Immunol. 123, 1548, (1979).
Shulman et al; Nature 276, 269, (1978).
Kohler and Howe et al; Eur. J. Immunol. 6, 292, (1976).
Wilde et al; Eur. J. Immunol. 10, 462, (1980).
Galfre et al; Nature 277, 131, (1979).
Kohler et al; Eur. J. Immunol. 6, 511, (1976).

*Primary Examiner*—Alvin E. Tanenholtz
*Assistant Examiner*—James Martinell
*Attorney, Agent, or Firm*—Oblon, Fisher, Spivak, McClelland & Maier

[57] ABSTRACT

A rat myeloma cell line which does not express an immunoglobulin chain, YB2/3.0.Ag.20, is prepared from the cell line Y3-Ag 1.2.3 via a hybrid myeloma cell line. This cell line, and variants thereof prepared by passaging and/or cloning the line, may be fused with immunocyte cells from an animal sensitized to an immunogen to produce hybrid myeloma cell lines which provide a source of monoclonal antibodies to said immunogen.

23 Claims, No Drawings

RAT MYELOMA CELL LINES

This invention relates to cell lines and to their use in the production of antibodies.

The production of monoclonal antibodies from cell lines derived by cell fusion techniques from an appropriate parental cell line has recently received considerable attention. Initially, the method employed one of several mouse myeloma cell lines as the parent cell line which was fused with cells from immunised mice or rats to give a hybrid myeloma which is then grown to thereby produce antibodies against the immunogen used in the immunisation. The particular advantage of this method is that it may be used for the production of highly specific antibodies using non-purified immunogens.

Although the method has provided an important new tool for use in immunology it had until recently suffered from certain limitations arising from the nature of the parental cell lines available. In 1979, however, a rat myeloma cell line, Y3-Ag 1.2.3, was described by Galfrè, Milstein and Wright (Nature 1979, 277, 131), this cell line being the subject of U.K. patent application No. 8,000,595 (published under the No. 2,039,948) and having been deposited with the C.N.C.M. at the Institut Pasteur on Jan. 9, 1979 in connection with that application (C.N.C.M. number I-078). The cell line Y3-Ag 1.2.3 itself possesses considerable advantages, as compared with the existing mouse myeloma cell lines, for use as a parent cell line in the preparation of monoclonal antibody producing hybrid myelomas (or hybridomas), but we have now prepared a new rat myeloma cell line which is a derivative of Y3-Ag 1.2.3 and which is even more suitable for this purpose.

Accordingly, the present invention comprises the rat myeloma cell line YB2/3.0.Ag.20.

Rat myeloma cell lines possess several advantages over the mouse myeloma cell lines. The in vivo cultivation of a hybrid cell line for the production of antibodies has certain advantages as compared with in vitro tissue culture methods including the significantly higher levels of antibody per ml which are obtained in animal serum as compared with a culture medium. The use of the rat for the in vivo culture is to be preferred to the use of the mouse on several counts, for example the yield of serum and ascitic fluid is higher, litters are generally larger, and rats may respond better than mice to antigenic stimulation. Moreover, rats are required for the production of monoclonal xenogenic anti-mouse and allogenic anti-rat antibodies but we have found that the hybrid cells produced by the combination of cells from immunised rats with a parent mouse myeloma cell line are not readily cultivated in either mice or rats. In addition, rat myeloma cell lines may have advantages in certain heterologous fusions such as those with rabbit or human cells.

The Cell line YB2/3.0.Ag.20 not only possesses the advantages described above, which are shared by the original rat cell line Y3-Ag 1.2.3, but also has additional properties of considerable value. Y3-Ag 1.2.3 produces and secretes a unique light chain of type kappa, code named S210, and it has been our experience that hybridomas produced using Y3-Ag 1.2.3 almost invariably also contain this light chain. Its presence in the hybridoma can, however, have disadvantages since antibody activity in respect of the immunogen used in its preparation is in general more fully expressed when only the immunoglobulin chains derived from the immunised animal, and usually designated as H and L, are present, immunoglobulin from the myeloma being capable of interfering with the binding characteristics of the antibody.

In the case of certain of the mouse myeloma parental cell lines, it has been possible to isolate directly therefrom mutants which do not express an immunoglobulin chain but, despite extensive investigations, a similar approach has not proved possible in the case of the Y3-Ag 1.2.3 cell line, and the cell line YB2/3.0.Ag.20 was obtained from Y3-Ag 1.2.3 by a somewhat unusual route. One of the fusion experiments in which the cell line Y3-Ag 1.2.3 has been used involved fusion with spleen cells from an A0 rat sensitized to human complement C3 to yield several anti-C3 antibody producing cell lines. One of these YB2/3HL, was unusual among hybridomas derived from Y3-Ag 1.2.3 in that it lacked the ability to express the kappa light chain. By a series of cloning experiments, described in detail hereinafter, it was found possible to select from YB2/3HL the cell line YB2/3.0.Ag.20 in which the ability to express the H and L chains was also missing, thereby giving a zero cell line which does not express an immunoglobulin chain.

Accordingly the present invention further comprises a rat myeloma cell line which does not express an immunoglobulin chain, said cell line being a derivative of the cell line Y3-Ag 1.2.3 which is prepared therefrom via a hybrid myeloma cell line.

Also included by the present invention is a process for the production of a rat myeloma cell line which comprises cloning a hybrid myeloma cell line derived from the cell line Y3-Ag 1.2.3 to isolate thereby a rat myeloma cell line derivative of Y3-Ag 1.2.3 which does not express as immunoglobulin chain. Such rat myeloma cell lines are commonly sensitive to hypoxanthine/aminopterin/thymidine (HAT) (Littlefield, Science, 1964, 145, 709) which facilitates the separation of parent cells from hybridomas which do not generally possess this property, and such sensitivity is often associated with 8-azaguanine resistance. The clones selected are thus preferably HAT sensitive in addition to non-Ig producing, and conveniently also 8-azaguanine resistant. The cell line YB2/3.0.Ag.20 was found to possess the properties of HAT sensitivity and 8-azaguanine resistance without the use of any positive steps to ensure that it possessed these properties. In other cases, however, it may be necessary to take positive steps to obtain a cell line possessing these properties, for example by growing hybridoma cells from the fusion of Y3-Ag 1.2.3 in a medium containing 8-azaguanine and selecting for cells which are resistant to this compound (as indicated above HAT sensitivity is often associated with 8-azaguanine resistance and the latter property is more readily selected for).

The cell line YB2/3.0.Ag.20 has markers of the two rat types used in its production, i.e. Lou (Y3-Ag 1.2.3 myeloma) and A0 (human complement C3 sensitized spleen cells), although the latter marker appears to be expressed only weakly. The cells have the same general morphology as Y3-Ag 1.2.3, which in turn has the same general morphology as its parent 210.RCY3.Ag1, but the cells (and generally also the hybrid cells derived therefrom) are larger and more rounded than Y3-Ag 1.2.3 cells. YB2/3.0.Ag.20 cells (and generally also the hybrid cells therefrom) are, however, smaller and less round than cells of the mouse myeloma cell line NSI/-

1A4-1 (and generally also as compared with hybrid cells therefrom). Cell adherence of YB2/3.0.Ag.20 to culture vessels, particularly those of a plastics material, is much less than that found with Y3-Ag 1.2.3 but similar to that found with NSI/1Ag4-1. The cell line YB2/3.0.Ag.20, like Y3-Ag 1.2.3, is resistant to 8-azaguanine (but at the higher level of 30 μg/ml), and it dies in medium containing HAT (Littlefield, Science, 1964, 145, 709). The cell line YB2/3.0.Ag.20 retains a good fusion ability, typically giving a level of efficiency of 1 per $10^6$ cells in fusion with rat spleen cells. Moreover, the clonability of the cells in soft agar is good and, indeed, is better than that of Y3-Ag 1.2.3 cells in as far as the clones are tighter thereby generally making hybridomas derived from YB2/3.0.Ag.20 easier to purify than those from Y3-Ag 1.2.3.

A stock of the cell line YB2/3.0.Ag.20 is held at the Medical Research Council's Laboratory of Molecular Biology in Cambridge and, additionally, the cell line was deposited with the C.N.C.M. at the Institut Pasteur in Paris on June 25, 1980 under C.N.C.M. number I. 126.

The cells YB2/3.0.Ag.20 may be grown in various forms of nutrient culture medium. Accordingly, the present invention extends to a cell culture system comprising cells of the cell line YB2/3.0.Ag.20 in a nutrient culture medium therefor. Such a cell-culture system is conveniently an in vitro one, the culture medium being an essentially synthetic medium although it may of course contain ingredients obtained from a natural source such as serum. Examples of such culture media are Dulbecco's modification of Eagle's minimum essential medium (available, for instance, from Gibco Biocult Ltd., Paisley, Scotland) with a serum supplement such as 10% v/v of heat inactivated horse serum or preferably of foetal calf serum. Alternatively, the cells may be conditioned to the use of a lower serum level than this or to the use of the Iscove modification containing no serum (Iscove and Melchers, Journal of Experimental Medicine, 1978, 147, 923). A supplement of antibiotic may conveniently also be used in the culture medium. With a minor period of conditioning the cells grown in such a medium can be grown in other media such as RPMI 1640 with foetal calf serum and various other media commonly used in cell culture and described in the literature of this art. In suspension culture a doubling time of about 24 hours is generally obtained, such a culture conveniently being fed three times a week by removing a proportion of the cells and medium and replacing these with fresh medium. In general, it is found that conditioning of the cells to growth in a medium of low serum content, for example one containing only about 5% v/v, or less, for example 2.5% v/v of serum supplement, is of value in preparing robust cells which readily accept the conditions to which they are exposed during fusion.

The cell line YB2/3.0.Ag.20 shows a good level of stability on storage in liquid nitrogen, and on in vitro culture through a number of generations of the line, although routine checks carried out from time to time are, as usual, advisable. It will be appreciated that certain properties of the cells such as fusion ability may even be capable of being improved by continued culture. Indeed, it is possible, for example through continued passaging and/or cloning, to obtain variants of the cell line which, whilst being substantially similar to YB2/3.0.Ag.20 in most respects, do possess certain altered properties, and a secondary use of the cell line in addition to its primary use as a parent cell line for use in fusions lies in the production of such variants. Such variants may arise spontaneously and be selected from the bulk of original YB2/3.0.Ag.20 cells by passaging in vitro, often followed by cloning, or particularly directly by cloning, the cloning being effected, for example, on soft agar. Such a process can, however, be rather tedious, involving the study of a large number of clones and the production of the variants is often more conveniently achieved by the use of conditions, particularly in passaging of the cells, which lead to adaption of the cells of the cell line with the production of variants thereof as described hereinafter.

Variants conveniently show a change in one or more of the properties of the cell line YB2/3.0.Ag.20 which are related to its use in the production of hybridomas. Such properties include fusion characteristics and growth characteristics, the latter being of particular interest where they have a bearing on the growth characteristics of the hybridoma. Variants of particular interest are those showing an enhancement of one or more of such properties and one particular type of variant of some especial interest is discussed hereinafter on page 10. It will be appreciated therefore that the present invention extends to further parent myeloma cell lines derived from the cell line YB2/3.0.Ag.20, particularly variants as described above.

The particular value of the cell line YB2/3.0.Ag.20, and of other parent cell lines according to the present invention is in the production of hybrid cell lines which can be used for the preparation of monoclonal antibodies. The procedures used for this purpose are broadly similar for the various parent cell lines, i.e. other zero cell lines derived from Y3-Ag 1.2.3 and variants of YB2/3.0.Ag.20, as well as YB2/3.0.Ag.20 itself but will for convenience be described hereinafter with particular reference to YB2/3.0.Ag.20. The method for the production of a hybrid cell line from the parent cell line comprises fusing spleen, lymph or other immunocyte cells (i.e. immunologically competent cells) sensitized to an immunogen with cells of the cell line. The sensitized immunocyte cells may be taken from various sources but it has been found that the best results are obtained using rat cells rather than cells from another host such as the mouse, human etc. As the YB2/3.-0.Ag.20 cell line has markers for both the Lou and AO rat, it is preferred, when subsequent production of antibody from the hybridoma by in vivo growth is contemplated, that the rat used to produce the immunocyte cells is either an AO or a Lou rat. With other parent cell lines according to the invention, as discussed hereinafter, the choice may be wider. Sensitization of the immunocyte cells may occur normally, i.e. through naturally occurring (or spontaneous) immunisation but it is preferred to produce sensitization through direct immunisation, the required immunogen being positively administered to the host animal in an immunisation procedure.

The fusion of suitable immunocytes with the cells of the cell line generally requires admixture in a suitable medium containing an agent which promotes the fusion. The present invention thus includes a system for the fusion of cells of the cell line YB2/3.0.Ag.20 and immunocyte cells, for example spleen cells from a mouse, or especially a human, and particularly a rat, in a nutrient culture medium therefor together with an agent which promotes the fusion of said cells. Such a culture medium is conveniently a synthetic one although it may of course, if desired, contain ingredients obtained from a natural source. However, such a possibility is less likely in this instance, it being preferred that serum is absent from the medium. Examples of such culture media are Eagle's minimum essential medium and its Dulbecco modification, as well as RPMI 1640 and various other media commonly used in cell culture and described in the literature of this art, an antibiotic supplement often being used as described above for culture of the cells. Although various fusion agents may be employed, for example a virus such as Sendai virus, polyethylene glycol is preferred, for example PEG 1500. Cell fusion with these agents is documented in the literature and illustrated in the accompanying Examples but, by way of guidance, it may be indicated that from about 40 to about 55% v/v of polyethylene glycol is often employed, the optimum concentration depending on molecular weight, for example about 50% v/v with PEG 1500, and that if desired dimethyl sulphoxide may be added to the polyethylene glycol. Hybridoma isolation may conveniently be assisted by replacement of the original medium with HAT medium which is toxic to the parent cell line but is not in general toxic to the hybrid line. Following this, cloning and sub-cloning are then conveniently employed to select a suitable hybrid or hybrids in the light of tests for antibody production thereby.

As indicated above, immunocyte cells sensitized to the required immunogen are obtainable by alternative methods. Thus, they may conveniently be obtained either by selecting naturally occurring immunocytes of the type required or by procedures described in the art comprising the administration to the animal (which term is used herein to include humans) of a series of doses of the immunogen together, where appropriate, with an adjuvant such as Freund's adjuvant, followed by harvesting of the spleen or other immunocyte cells. The use of naturally occurring immunocytes is of particular interest in relation to human immunocyte cells, where administration of the immunogen may be less attractive and the immunocytes produced naturally through an infection acquired by the patient may be more suitable. An area of particular interest in relation to natural immunocytes is the production of auto antibodies.

The invention is applicable to immunocytes from directly or naturally immunised animals sensitized against a wide range of immunogens including antigens such as proteins and glyco-proteins, oligo- and polysaccharides, liposaccharides, haptens and like, for example peptides, neuro-transmitters and hormones. Immunogens which are surface markers and which are derived from neoplastic material, particularly solid tumours, are of considerable interest but the invention may also be applied to bacterial and viral antigens and to immunogens derived from protozoa and fungi.

The present invention thus further includes cells being a hybrid between the rat myeloma cell line YB2/3.0.Ag.20, or other parent cell lines according to the present invention as discussed hereinbefore, and spleen or other immunocyte cells from an animal, for example from a mouse, or especially a human, or more particularly from a rat, sensitized to an immunogen.

The hybrid cells may conveniently be maintained by culture in the same general type of culture medium as the parent YB2/3.0.Ag.20 cells and as discussed hereinbefore.

The production of antibodies by the cell lines of the present invention may be effected through culturing a cell line in either an in vitro or an in vivo culture medium therefor. The present invention thus includes a process for the production of antibodies which comprises culturing hybrid cells derived from the cell line YB2/3.0.Ag.20, or other parent cell line according to the present invention, in an in vitro or in vivo culture medium therefor and thereafter isolating the antibodies from said medium.

The choice between an in vitro and an in vivo procedure depends on various factors. Thus in vitro culture may be indicated where the use for which the antibodies are required is of an immunological rather than a chemical nature and the presence of rat immunoglobulin contaminants from in vivo growth in a rat is undesirable. In vitro growth also has the advantage that the strain of rat from which the immunocyte cells are obtained is not of the significance it is in the case of in vivo growth. Moreover, there may be cases where the hybridoma cells will not grow in vivo. In vivo culture does, however, have the particular advantage that significantly higher levels of antibody per ml are generally obtained (in serum and/or ascitic fluid) as compared with an in vitro culture medium. In vivo culture is preferably carried out in a rat and in the case of the cell line YB2/3.0.Ag.20, which as mentioned previously is conveniently fused with immunocytes from an A0 or Lou strain of rat where in vivo culture of the resultant hybridoma for the production of antibody is contemplated, the rat is preferably a Lou×A0 hybrid although less ready growth in an A0 or Lou pure strain of rat may be possible. Additionally, it may be possible to affect growth of a hybridoma in rats of an incompatible strain by the use of irradiation and/or of immunosuppressive drugs.

When the parent myeloma cell line derives from a single strain of rat, such as the strain Lou in the case of the line Y3-Ag 1.2.3, then a particular advantage accrues in that any pure strain of rat may be used to provide the immunocyte cells which are fused with the parent cell line to produce the hybridoma and ready in vivo growth of the hybridoma should occur in a hybrid of the strains corresponding to the derivation of the parent cell line and of the immunocytes. Accordingly, a particular form of a variant of the cell line YB2/3.0.Ag.20 such as is referred to hereinbefore is one in which the cell line is adapted to growth in a pure strain of rat, particularly A0 or especially Lou, with the marker for A0 having been lost or masked in the latter case. A preferred procedure for adapting the cell line YB2/3.0.Ag.20 in this way is to passage it through a plurality of rats, for example at least 5 and particularly about 10, which are of the strain to which the line is to be adapted. In this way it is possible to adapt the cell line from the mode of growth seen initially in the first few rats of the series, where eventually regression of the tumour induced by the cell line occurs, to that seen in the later rats of the series where ready growth occurs without regression. The tumour cells isolated from the final rat may then be cultured, and cloned if desired to provide a variant of the cell line YB2/3.0.Ag.20 adapted to show an enhanced property in respect of the range of rat species which may be used with convenience to provide immunocytes for fusion with the variant. Various adapted cell lines of this type may be prepared, preferred examples being selected for their retention or even improvement of the fusion characteristics of YB2/3.0.Ag.20.

In the case of an in vitro system, the culture medium used may be similar to that described above in relation to a cell culture system but the serum levels are preferably as low as possible, for example being 5% v/v or below, preferably no more than about 2.5% v/v and conveniently as low as 0.5% v/v. Alternatively the Iscove serum-less modification may be used. The cells may conveniently be allowed to grow well beyond logarithmic phase, thereby sacrificing final viability to achieve maximum final density. A short period of growth at the cell stationary phase is also desirable as this improves the final yield of antibody. Examples of suitable tissue culture procedures of antibody production are massive growth in spinner containers and other known mass culture procedures which are well documented in the art. The in vivo procedure conveniently comprises the inoculation of a rat to produce a solid or ascitic tumour. Prior to inoculation the rat may conveniently be immunosuppressed and/or treated with a drug such as a pristane to induce ascitic fluid secretion. After a suitable period of growth of the tumour the animal is killed and the ascites and/or serum are collected for isolation of the antibody, optionally following a period of collection of ascitic fluid from the living animal in the case of as ascitic tumour. An ascitic tumour thus has the potential of producing a higher amount of fluid but the value of this technique will depend upon the concentration of antibody present in the ascites and/or serum. Isolation of the antibody from either an in vitro or an in vivo procedure is conveniently effected by procedures described in the art including precipitation, dialysis, chromatography including the use of immuno-adsorbents, and the use of membrane filters.

The present invention thus includes a method for the production of monoclonal antibodies which comprises inoculating an animal and particularly a rat with hybrid cells derived from the cell line YB2/3.0.Ag.20 or other parent cell lines according to the present invention, thereby causing a solid or ascitic tumour to grow in the rat, and thereafter isolating the antibodies from the serum and/or ascitic fluid of the rat.

It will be appreciated that the present invention extends to antibodies whenever prepared using hybrid cells derived from the cell line YB2/3.0.Ag.20 or other parent cell lines according to the present invention. Such antibodies have various applications in therapeutics and particularly in diagnostics, and also in such procedures as affinity chromatography. One example of monoclonal antibodies which may be produced is antibodies to various tumour cells of human origin which recognise sub-populations of human cells and which are of potential use in haematological diagnosis. Another type of use is exemplified by the use of an antibody against a naturally occurring substance such as a protein for the purification of that substance.

The invention is illustrated by the following Examples

EXAMPLES

Example 1

Preparation of the cell line YB2/3.0.Ag.20 from the hybrid cell line YB2/3HL

Cells of the hybrid cell line YB2/3HL derived from the cell line Y3-Ag 1.2.3 were taken from a culture in a medium based on Dulbecco's modified Eagle's medium (this medium is identified herein as DMM and contains the ingredients listed in the footnote) supplemented with 10% v/v of foetal calf serum [FCS; selected from different batches (Sera-Lab Catalogue No. 5-000-1a)] and cloned in soft agar essentially as described by Cotton et al, European Journal of Immunology, 1973, 3, 136. A total of 116 random clones were cultured and the culture supernatant was screened for production of rat Ig by indirect agglutination of sheep red blood corpuscles (SRBC) which had been coupled with chromium chloride to anti-rat IG raised in sheep (Köhler et al, European Journal of Immunology, 1976, 6, 292). In each case the supernatant was mixed with the SRBC and, after 10 minutes standing, free anti-rat Ig was added, the presence of rat Ig in a supernatant then resulting in agglutination. From the 116 clones, 3 were selected as being negative or only weakly positive in respect of rat immunoglobulin production, these 3 clones being identified as P1.F11, P2.G11 and P2.H12. Extracellular and intracellular [$^{14}$C]-lysine incorporation by the three clones was then studied by incubation in DMM-5% FCS (the FCS used having been dialysed) in which the usual lysine content of the medium was replaced with [$^{14}$C]-lysine, the supernatants being analysed as described by Köhler and Milstein, European Journal of Immunology, 1976, 6, 511, using sodium dodecyl sulphate polyacrylamide electrophoresis (SDS-PAGE) after total reduction.

The DMM was a commercial preparation of Dulbecco's modified Eagle's medium to which certain supplements were added and contained the following ingredients:

500 ml Dulbecco MEM (with 4500 mg glucose/liter and without sodium pyruvate)—Gibco-Biocult Catalogue No. 320-1965.

5 ml Sodium pyruvate MEM (100 mM)—Gibco-Biocult Catalogue No. 320-1360

10 ml Penicillin/streptomycin (5000 units penicillin/500 mcg streptomycin/ml)

(The medium has a NaHCO$_3$ content of 3,700 mg/liter and a pH of 7.2 to 7.5) The results obtained are shown in the Table:

| Clone (YB2/3HL) | Extracellular Incorporation | Intracellular Incorporation |
| --- | --- | --- |
| P1.F11 | very weak HL | HL |
| P2.G11 | no chains | H |
| P2.H12 | no chains | L |

In order to investigate the 3 clones further, each was screened by intracellular fluorescence microscopy using fluorescein isothiocyanate rabbit anti-rat Ig (Bradstock, et al, Journal of National Cancer Institute, 65, No. 7, 81) and the clone P2.G11 emerged as the most promising for the isolation of a zero cell line as it showed a population of approximately 60% negatives to 40% strong positives.

The clone YB2/3HL P2.G11 was therefore cloned in soft agar and 43 resulting clones were screened by intracellular fluorescence microscopy with the result that 22 clear negatives were found together with 9 clear positives and 12 mixed clones or clones which were unclear. The 22 clones which were negative on screening by intracellular fluorescence microscopy were then screened further and the clone YB2/3HL P2.G11.16(0) was selected as showing the presence of no chains on intracellular [$^{14}$C]-lysine incorporation followed by SDS-PAGE analysis. It was not necessary to adapt the cells to 8-azaguanine as they were found already to be resistant to 30 µg/ml 8-azaguanine. These cells, YB2/3HL.P2.G11.16(0) Ag, were then cloned in soft agar in the presence of 30 µg/ml of 8-azaguanine, and clones were selected on the basis of tight growth of the clone. Clone YB2/3HL.P2.G11.16(0) Ag.20 was further selected in view of its fast growth rate and a sample was tested for HAT sensitivity, the cells dying within 3 days in medium containing HAT.

The YB2/3HL.P2.G11.16(0) Ag.20 cells thus showed characteristics appropriate to use as a parent myeloma cell line in fusions leading to monoclonal antibody producing hybridomas and constitutes the cell line YB2/3.-0.Ag.20. The cells were taken from the agar and transferred to the 2 ml wells of Linbro plates to which had been added DMM medium containing 20% v/v FCS. The cells were then grown up and gradually conditioned both to grow in larger culture vessels, and to a lower serum level by the usual procedure of reducing the serum level of the replacement medium fed to the culture (culture being at 37° C. in a 10% v/v $CO_2$/90% v/v air atmosphere). In this way, the cells were conditioned to growth in 2.5% v/v FCS 2.5% v/v heat inactivated horse serum and then to 5% v/v FCS and finally 2.5% v/v FCS, and were ultimately cultured in a liter spinner flask at 37° C. in an atmosphere of 10% v/v $CO_2$/90% v/v air and 95% humidity).

Frozen samples of the cell line, including those deposited in the culture collection, were prepared from exponentially growing cells at not more than $5\times10^5$ cells/ml. An amount of medium containing greater than $1\times10^7$ cells was centrifuged at 600 g for 7 minutes. The cell pellet was cooled to 4° C. and then suspended in 90% v/v FCS-10% dimethyl sulphoxide at a density of $5\times10^6$ cells/ml. 1 ml of this suspension at 4° C. was placed in an ampoule which was then sealed and frozen by lowering the temperature from 4° C. at a temperature gradient of 1° C./hour. When the cells have reached $-50°$ C., they are immersed in liquid nitrogen. To recover cells from such frozen ampoules, the content of an ampoule is brought rapidly to a temperature of 4° C. and is then immediately diluted to a volume of 20 ml with cold (4° C.) DMM-10% v/v FCS. The cells are then centrifuged at 600 g for 7 minutes and are resuspended into cultures of 2 ml each containing ½, ¼, ⅛, 1/16 and 1/32 pelleted cells. Following this the cultures are allowed to grow at 37° C. in an atmosphere of 10% v/v $CO_2$—90% v/v air, further growth being carried out as described hereinbefore for the cells prior to freezing. To prepare new frozen stocks it is necessary to grow the cultures thereby obtained for a minimum time of one week after thawing and a maximum of three weeks. During this time the cells should be growing exponentially with a doubling time of about 24 hours.

Source of the hybrid cell line YB2/3HL

The YB2/3HL cells were prepared as follows. A suspension of inulin (British Drug Houses) in phosphate buffered saline (100 mg/ml) was sonicated for 1 minute and 0.5 ml of the suspension was then treated with 10 ml of normal human serum [brought to 10 mM with ethylene glycol bis(β-aminoethyl ether) N,N'-tetraacetic acid (EGTA) and to 7 mM in Mg with $MgCl_2$] for 15 minutes at 37° C. to allow activation of the alternative complement pathway and fixation of C3 to inulin. The suspension was washed using centrifugation in physiological saline, in 2M NaCl and again in physiological saline before being made up to the original volume of 1 ml with physiological saline.

The 1 ml of antigenic complement preparation was emulsified with 50 µl of normal rat serum of 250 µl of a pencillin/streptomycin solution (5000 units penicillin/500 mcg streptomycin/ml) in ca 1 ml of Freund's complete adjuvant (CFA) to give a final volume of 2.4 ml. Two A0 rats were each given 0.1 ml of this preparation by intramuscular injection at each of four sites (total of 0.4 ml per rat). Three weeks later each rat was given 0.5 ml of a similar antigenic preparation in the absence of CFA but with $5\times10^9$B. pertussis by intraperistoneal injection. Four weeks later each rat was given a further 0.5 ml amount of the antigenic preparation, without any form of adjuvant, by intravenous injection and during the succeeding month five further similar intravenous injections were administered.

The rats were killed on the third day following the last i.v. injection. In the case of each rat, its spleen was removed under sterile conditions, placed in a small Petri dish on ice in 5 ml of freshly prepared DMM medium containing no serum supplement. After some cuts had been made in the spleen, it was transferred to a 10 ml plastic round-bottomed tube containing 4 ml of the serum-free DMM medium as described hereinbefore, and was disrupted with a Teflon pestle of loose fit (2 mm clearance). The resulting mixture was left on ice for 1 minute and the top 3.5 ml was then transferred to a plastic universal tube. The remainder of the disrupted spleen was washed with 5 ml of DMM and the mixture allowed to stand for 1 minute to allow major debris to settle. the supernatant was then decanted from such debris and added to the cells in the universal tube. This tube was topped up with DMM and was spun at 600 rpm for 7 minutes in a bench centrifuge. The supernatant was then decanted off, and the cells were resuspended in DMM. An aliquot of this suspension containing $10^8$ cells was mixed in a 50 ml conical centrifuge tube with $10^7$ washed Y3-Ag 1.2.3 cells from the stock held at the MRC's Laboratory of Molecular Biology in Cambridge. DMM medium was then added to the cell mixture and the whole was centrifuged.

The tube containing the drained cell pellet was placed in a 37° C. water bath and tapped gently. 0.8 ml of 50% w/v polyethylene glycol (PEG) 1500 in DMM at 37° C. was added to the cells over a period of 1 minute, a pipette being used to effect gentle mixing. Gentle mixing was continued for a further 1 minute and 2 ml of DMM medium was then added over a period of 2 minutes, followed by 8 ml of DMM over 3 minutes, and a further 10 ml of DMM which was added dropwise. The cells were spun, resuspended gently first in a few drops and then in 25 ml of prewarmed (37° C.) DMM medium to which a supplement of 20% v/v of foetal calf serum (FCS) from different batches (Ser-Lab catalogue No. 5-000-1a) had been added. The volume was then made up to 50 ml with the same prewarmed medium. (The FCS used at this stage and during the following period of incubation was heat inactivated at 56° C. for 30 minutes.)

The cell-containing media obtained from two rats were distributed in 96×2 ml wells of Linbro plates and about $1\times10^5$ washed spleen cells in 1 ml of the same medium were added to each well as feeder and the whole was incubated at 37° C. Next day 1 ml of the 2 ml of medium was removed from each well and replaced with 1 ml of DMM medium containing 20% FCS and also HAT (Littlefield, Science, 1964, 145, 709). Incubation was continued at 37° C. for a period of two weeks, replacement of half the medium with the HAT medium being similarly effected on the next two days after the initial replacement and at 2–3 day intervals thereafter.

Active growth was observed in 80 of the wells after the two weeks, such growth being taken as showing the presence of hybrid myeloma. The spent medium of each of the 80 cultures was tested for antibody production by an indirect binding assay as follows. A complex was made essentially according to the procedure of Lachmann and Hobart, 1978, Complement Technology, Chapter 5A of the Handbook of Experimental Immunology, editor D. M. Weir (Blackwall Scientific Publications) by treating sheep antibody carrying erythrocytes (EA) with yeast treated human serum (R3) at 37° C. followed by washing. This intermediate form of a complex (designated EAC) has C3b, C3bi and some C3d on its surface but has no C5 or later components on it as the R3 was obtained from a 'non-reactor' serum. Both EA and EAC were treated with dilutions of the spent medium from each well, then washed and incubated with [$^{125}$I]-labelled anti-rat immunoglobulin antibody. After further washing, the radio-activity of the cells was measured. Only three of the 80 cultures showed convincing antibody producing activity as measured by this indirect binding assay and one of these cultures deriving from one of the two rats contained the hybrid myeloma YB2/39.

The hybrid myeloma YB2/39 was cloned in soft agar using a procedure essentially as described by Cotton et al, ibid. Cloning was carried out at serveral cell densities and clones were selected from the lowest clone densities. The cloning efficiency at this first cloning stage was about 10% but the proportion of active clones as first isolated was 100% (21/21). Clone 39-11 was selected and cloned in soft agar to give 4/4 positive clones from which clone 39-11-1-7 was selected and cloned in soft agar to give a clone 39-11-1-7 which constitutes the cell line YB2/3HL. The cells were taken from the agar of a plate containing a low number of clones/plate (<100), the number of cells per clone being about 100. The cells were transferred to the 2 ml wells of Linbro plates to which had been added 1 ml of DMM containing 20% v/v FCS. The cells were then grown up in the DMM containing 20% v/v FCS in the usual manner and, as growth became vigorous, the serum concentration of the medium used to feed the cultures was lowered to 10% v/v. Larger cultures were made by transferring the cells to flat bottom tissue culture bottles of various sizes, the cells being grown at 37° C. as suspension cultures in the usual fashion with the bottles being tightly sealed to enclose an atmosphere of 10% v/v $CO_2$ in air.

EXAMPLE 2

Production of a hybridoma by the fusion of the cell line YB2/3.0.Ag.20 with spleen cells from a rat hyperimmunised with yeast tubulin A rat of the Lou strain was immunised according to the following schedule:
day 1: 20 µg yeast tubulin in Freund's complete adjuvant injected intraperitoneally (i.p.);
day 22: 20 µg yeast tubulin in Freund's incomplete adjuvant injected i.p.;
day 53: as day 22;
day 85: 20 µg yeast tubulin injected intravenously (i.v.).

On day 89 the rat was killed, and its spleen removed under sterile conditions and prepared for fusion as described on page but employing DMM medium which contains a 2% v/v FCS serum supplement, only the final topping up followed by spinning at 600 rpm for 7 minutes and the subsequent resuspension being effected with DMM medium containing no serum supplement. An aliquot of the resuspended spleen cells containing $10^8$ cells was mixed with $6 \times 10^7$ cells of the cell line YB2/3.0.Ag.20 in the same medium. The mixture was centrifuged in a 50 ml plastic conical tube at 600 g for 7 minutes and the supernatant was then removed and the cell pellet disrupted by gently tapping the bottom of the tube. Further operations were performed at about 37° C. A 1 ml pipette containing 1.0 ml of 50% polyethylene glycol (PEG) 1500 (freshly prepared or kept in the dark) in DMM medium (pH 7.6–7.8 as indicated by phenol red) was used to suspend the cells gently while the solution was added over a period of 1 minute. The suspension was kept at 37° C. for 1 minute and 1 ml of DMM medium was added over another period of 1 minute. A further 20 ml of DMM medium was then added over a period of 5 minutes and the cells were centrifuged and gently resuspended in DMM medium containing 20% v/v FCS to give a total volume of 25 ml.

The suspension was distributed as follows in 0.5 ml amounts in Linbro BCL-5041 trays containing $48 \times 2$ ml wells. 18 ml of the 25 ml original volume were distributed into 36 wells and the remaining 7 ml were diluted to 14 ml (this, and subsequent dilutions were effected with DMM medium containing 20% v/v FCS). 6 ml of the 14 ml were distributed into 12 wells and the remaining 8 ml were diluted to 16 ml. 6 ml of the 16 ml were distributed into 12 wells and the remaining 10 ml were diluted to 20 ml. 18 ml of the 20 ml were distributed into 36 wells and the remaining 2 ml were discarded. Each of the 96 wells was made up to a volume of 2 ml with DMM medium containing 20% v/v FCS. The cells were then cultured and after 24 hours one half of the medium was replaced with DMM medium containing 20% v/v FCS and also HAT (Littlefield, Science, 1964, 145, 709). This operation was repeated on the two subsequent days and then every 2 days.

Vigorous growth in a well after 15–20 days was taken as showing a successful hybrid clone(s). A total of 52 wells showed hybrid growth (36/36, 2/12, 3/12 and 9/36 in order of increasing dilution).

An analysis of the original, undiluted cultures was made at this stage, a high proportion of the 36 growing cultures being analysed by SDS-PAGE (technical reasons prevented analysis of all the cultures). Of the 28 cultures analysed, the average number of hybrid clones per culture was 1 and 90% of the hybrids secreted Ig heavy chain (the detailed analysis being: no heavy chain, 3; µ heavy chain only, 24; γ heavy chain only, 1; both µ and γ heavy chain, 0).

The spent medium of each hybrid culture was also tested in a binding assay (Jensenius and Williams, European Journal of Immunology, 1974, 4, 91) using the following procedure, 25 µl of a 50 µg/ml yeast tubulin solution were placed into the wells of a Sterilin flat bottomed 96 well microtitre plate which was then kept overnight at 4° C. The yeast tubulin was then removed and to each well was added 100 µl of 0.5M potassium phosphate buffer of pH 7.5 containing 0.1M Hepes of pH 7.2, 0.15M NaCl, 0.8% v/v bovine serum albumin and 0.1% v/v sodium azide, the plate then being left for 1 hour at room temperature. The wells were washed with 100 μl of the same buffer solution (2×) and 25 μl of the spent medium was added and the plate kept for 1 hour at 4° C. After washing (2×) with phosphate buffered saline, 25 μl of [$^{125}$I]-sheep anti-rat Ig was added to each well (ca. $10^5$ counts per well) and the plate was kept for a further 1 hour at 4° C. The wells were then washed with phosphate buffered saline (3×) and then with 100 μl of 2N aqueous sodium hydroxide solution. A count of radioactivity levels was then made, take up of [$^{125}$I]-activity by a well indicated a positive reaction. Of the 52 wells, 6 wells gave a positive reaction in this test.

Four of the six positive cultures, designated YOL1/5, YOL1/19, YOL1/34 and YOL1/38 (YOL1/34 having a particularly high affinity for tubulin) were cloned on soft agar using a procedure essentially as described by Cotton et al, ibid. In each case one or more of the clones obtained were re-cloned on soft agar. The clones were tested for yeast tubulin binding after the first and second clonings by a similar form of assay to that used previously with the following results:
YOL1/5
　1st 6 clones tested, all positive
　2nd 23 clones tested, 22 positive
YOL1/19
　1st 10 clones tested, 9 positive
　2nd 22 clones tested, 17 positive
YOL1/34
　1st 18 clones tested, 3 positive
　2nd 12 clones tested, 12 positive
YOL1/38
　1st 9 clones tested, 9 positive
　2nd 11 clones tested, 11 positive In the case of the culture YOL1/34, one of the 3 positive clones (YOL1/34.10) was re-cloned, resulting in 12 positive clones (YOL1/34.10.1 to YOL1/34.10.12). It will be seen that the initial instability of the culture in respect of positive antibody production, as indicated in the results of the first cloning, has been overcome in the second cloning. All of the clones YOL1/34.10.1 to YOL1/34.10.12, like the original culture, produced antibody having a very high binding affinity for tubulin.

Note

In an exactly comparable experiment using the same spleen cells the parent rat myeloma cell line Y3-Ag.1.2.3 gave a higher level of wells which were positive for hybrid growth but only the same number of wells which were positive in the direct haemagglutination assay, thereby suggesting a higher efficiency for YB2/3.0.Ag.20.

EXAMPLE 3

Production of a hybridoma by the fusion of the cell line YB2/3.0.Ag.20 with human spleen cells Normal human spleen cells were prepared for fusion exactly as described in Example 2 and an aliquot of $10^8$ spleen cells in DMM medium in the absence of any serum supplement was mixed with $6 \times 10^7$ cells of the cell line YB2/3.0.Ag.20 in the same medium. The mixture of cells was then treated to effect fusion thereof according to the procedure described in Example 2 to give a similar 25 ml volume of a suspension of cells in DMM containing 20% v/v FCS as described therein.

The suspension was distributed in 0.5 ml amounts into 48 wells of a Linbro BCL-5041 tray and each of the wells was made up to a volume of 2 ml with DMM medium containing 20% v/v FCS. The cells were then cultured and after 24 hours one half of the medium was replaced with DMM medium containing 20% v/v FCS and also HAT (Littlefield Science, 1964, 145, 709). This operation was repeated on the two subsequent days and then every 2 days.

Vigorous growth in a well after 15–20 days was taken as showing a successful hybrid clone(s) and all of the 48 wells were found to show hybrid growth. The spent medium of each hybrid culture was tested in a procedure relying upon inhibition of the agglutination of sheep red blood cells. The cells used were coated with human gamma globulin and were tested for agglutination with monoclonal anti-human kappa Ig and monoclonal anti-human gamma Ig. The presence of free human Ig will block binding with the antibody and such blockage was found to occur for all 48 of the cultures indicating them to be positive for human Ig.

Although the fusion procedure using the cell line YB2/3.0.Ag.20 with human spleen cells thus provided to be successful, it was found that the resultant hybridomas obtained in this particular procedure lost their ability to produce antibody after about 2 weeks.

EXAMPLE 4

Production of a hybridoma by the fusion of the cell line YB2/3.0.Ag.20 with human peripheral blood lymphocytes (A) The procedure of Example 3 was followed replacing the normal human spleen cells by human peripheral blood lymphocytes from a naturally rhesus negative (anti-D positive) patient who had been further sensitized by the administration of rhesus positive cells. A total of 96 cultures are carried out in Linbro BCL-5041 trays and, of these, 34 showed vigorous growth indicating the presence of a hybrid clone. None of the 34 hybrids was anti-D positive but one was found to be positive for human kappa Ig in the test described in Example 3.

The anti-human kappa Ig producing hybridoma was cultured for 2 months in DMM medium containing FCS at a level which was reduced from an initial 20% v/v to a final 2.5% v/v, and was then cloned on soft agar, the procedures used being as described in Example 1. Of the 20 resultant clones, 18 were positive for human kappa Ig and, following adaption of these clones to 8-azaguanine (the clones produced also being HAT sensitive), 12 of the 18 remained positive. One of these 12 clones has been maintained for 6 months in spinner culture in DMM medium containing FCS at a level which was reduced from an initial 20% v/v to a final 2.5% v/v, and still remains positive.

(B) In a variant of the procedure described above, the peripheral blood lymphocytes are stimulated, prior to fusion, with poke weed mitogen which is an agent recognised to enhance immunoglobulin production. This procedure, applied to a fraction of the same sample of the lymphocytes used in (A), led to the production of a total of 37 hybrids, of which 23 were positive for human Ig in a broad spectrum test based upon the use of sheep red blood cells coated with protein A. The cells were incubated in turn with rabbit anti-human Ig and then with culture medium supernatant, followed by treatment with guinea pig complement which will lyse the red blood cells if human Ig has been introduced in the system by the supernatant. However, although the high proportion of 23/37 positives was obtained, none of the hybridomas was able to maintain its ability to produce antibody for more than one month.

EXAMPLE 5

In vivo production of a monoclonal antibody against yeast tubulin

YOL1/34.10.1 cells produced as described in Example 2 are grown as tumours in F1 hybrid (Lou×A0) rats, the procedure utilising a single rat initially but followed by transplantion of the resultant tumour from this rat into others from which the tumour is transplanted twice more, so that the procedure utilises in all four "generations" of rats.

In three separate experiments utilising totals of rats in all four "generations" combined at 17, 19 and 9 rats, respectively, the cells ($5 \times 10^7$) were administered by subcutaneous injection. In each rat a solid tumour became evident at the site of injection after about 10 days and when the animal began to show signs of distress it was sacrificed by total bleeding from the arteries after total anaesthesia (in some cases, as mentioned above, some of the tumour cells were used for transplantations into a rat of the next "generation"). The collected blood was allowed to clot for 30 minutes at 37° C. and the serum was then cleared by centifugation. In the three experiments the yields of pooled blood were as follows: 135 ml from 17 rats, 169 ml from 19 rats and 100 ml from 9 rats (the yields of serum being about two thirds of these amounts).

In a fourth experiment the tumour was grown as an ascitic tumour utilising a total in all four "generations" combined of 11 rats. The cells ($5 \times 10^7$) were administered to the rats by intraperitoneal injection, following the intraperitoneal injection about 2 weeks previously of 0.5 ml of pristane, and on sacrifice both blood and ascitic fluid (after surgical exposure of the abdominal cavity) were collected as a source of antibody. The combined yield of pooled serum and ascitic fluid was 271 ml.

Although the yield of antibody-containing fluid was higher per rat for the intraperitoneally injected, ascitic tumour rats, the antibody titres were generally lower in the fluid from these animals, a typical titre being between $5 \times 10^5$ to $10^6$ for the subcutaneously injected, solid tumour rats, whilst only a few of the ascitic tumour rats produced titres as high as this. The IgG content for the solid tumour rats was typically between 10 and 15 mg/ml whilst it was often less than 8 mg/ml for the ascitic tumour rats.

The serum or serum ascitic fluid obtained may be purified further to a degree appropriate to their intended use by means of known procedures described in the art, for example by the procedures described in Example 6.

EXAMPLE 6

In vitro production of a monoclonal antibody

Hybridoma cells, for example as produced in Example 2, are conditioned to grow in the presence of a minimal amount of serum (0.5% v/v). Once conditioned, the cells are grown in 5 liter spinner flasks containing DMM medium-supplemented with 0.5% v/v of foetal calf serum and an atmosphere of 10% $CO_2$-90% air. The cells are grown until they reach the stationary phase[1] when the suspension typically contains from 10 to 50 μg of antibody per ml.

In order to purify the antibody preparation, ammonium sulphate is added to the suspension to produce 50% saturation and the resulting precipitate is collected. The precipitate is dissolved in a minimum volume of phosphate buffered saline and the solution is dialysed against the same medium to produce a purified antibody preparation.

(1) In a second variant the cells are grown in logarithmic phase with a minimum serum concentration and are then directly diluted with medium which contains no serum but does contain growth additives such as those recommended by Iscove.

(2) In a third variant the purification procedure is continued using DEAE chromatography or immunoadsorbents, for example anti-rat immunoglobulin, or alternatively the procedure described is replaced by the use of membrane filters.

EXAMPLE 7

Production of an adaption of the cell line YB2/3.0.Ag.20

A quantity of $10^8$ to $10^9$ YB2/3.0.Ag.20 cells in normal saline is administered by subcutaneous injection to a Lou rat when a solid tumour gradually develops at the site of injection. At the first sign of the tumour regressing the rat is sacrificed and the tumour excised. The tumour is disrupted and approximately $10^8$ to $10^9$ of the tumour cells in normal saline are administered by subcutaneous injection to a second Lou rat. This procedure is repeated until the cells have been grown in turn in a total of ten Lou rats. Although signs of regression of the tumour are detected in the first few rats, these signs are absent from the later rats as the cell line becomes better adapted to growth in the Lou rat. In these later rats the animal is sacrificed when it begins to show signs of distress. The increasing ease of growth of the tumour is illustrated by the shortened periods of growth in each rat after the first few, the dates of injection of the ten rats being as follows: 9th September, 16th October, 28th October, 12th November, 20th November, 28th November, 6th December, 15th December, 22nd December and 31st December.

Tumour cells from the tenth rat were put into DMM containing 10% v/v FCS and were then disrupted by pushing through fine nylon mesh with a plunger to give a cell suspension. The suspension was distributed at a variety of dilutions into DMM containing 20% v/v FCS and subcultured repeatedly in Linbro plates gradually reducing the concentration of FCS in the medium.

After a period of 3 weeks a sub-culture growing in DMM containing 2.5% FCS was obtained, designated YB0, and this cell line has been maintained in spinner culture in DMM/2.5% v/v FCS using an exactly similar procedure to that described in Example 1 for YB2/3.0.Ag.20 itself. The properties of the cell line YB0 are substantially similar to those of YB2/3.0.Ag.20 but it is adapted to ready growth in pure Lou as well as hybrid Lou×A0 rats, the A0 marker apparently having been lost or fully suppressed in this cell line.

We claim:

1. The rat myeloma cell line YB2/3.0.Ag.20.

2. A rat myeloma cell line being a variant of the cell line YB2/3.0.Ag.20 prepared by passaging and/or cloning cell line YB2/3.0.Ag.20.

3. A hybrid myeloma cell line derived from a parent myeloma cell line according to claim 1 or 2.

4. A hybrid myeloma cell line, prepared through the fusion of YB2/3.0.Ag.20 or a variant thereof prepared by passaging and/or cloning YB2/3.0.Ag.20, with immunocyte cells from an animal sensitized to an antigen.

5. An in vitro cell culture system comprising cells according to claim 1 or 2 in a nutrient medium therefor.

6. An in vitro cell culture system according to claim 5, comprising a rat myeloma cell line having the characteristics of the cells YB2/3.0.Ag.20 in a nutrient medium therefor.

7. A cell fusion system which comprises cells of a cell line according to claim 2 or 3 and immunocyte cells from an animal sensitized to an immunogen in a nutrient culture medium therefor with an agent which promotes the fusion of said cells.

8. A cell fusion system according to claim 7 in which the cell line is YB2/3.0.Ag.20.

9. A cell fusion system according to claim 8, in which the immunocyte cells are spleen cells.

10. A cell fusion system according to claim 8, in which the immunocyte cells are rat cells.

11. A cell fusion system according to claim 8, in which the agent which promotes fusion is polyethylene glycol.

12. A cell fusion system according to claim 7, which comprises cells of the cell line YB2/3.0.Ag.20 and spleen cells from a rat sensitized to an immunogen in a nutrient culture medium therefor together with polyethylene glycol.

13. A process for producing a rat myeloma cell line which comprises passaging and/or cloning YB2/3.0.Ag.20.

14. A process according to claim 13 in which said rat myeloma cell line is obtained by passaging YB2/3.0.Ag.20 in vivo.

15. A process according to claim 14, in which the passaged cells are cloned.

16. A process according to claim 14, in which the cell line is passaged through a plurality of rats.

17. A process according to claim 16, in which the rats are of the Lou strain, the variant having the ability to grow readily in a pure Lou strain rat in addition to an A0×Lou hybrid rat.

18. A process according to claim 13, in which the rat myeloma cell line is obtained by cloning a plurality of cells of the cell line.

19. A process for producing a hybrid myeloma cell line which comprises fusing cells of a cell line according to any of claims 1 or 2, with immunocyte cells from an animal sensitized to an immunogen using an agent which promotes the fusion of said cells.

20. A process according to claim 19, in which the animal from which the immunocyte cells are derived is a rat.

21. A process for the production of antibodies which comprises culturing cells of a hybrid myeloma cell line according to claim 5 in an in vitro or in vivo culture medium therefor and thereafter isolating the antibodies from said medium.

22. An antibody production process which comprises preparing a hybrid myeloma cell line by the fusion of cells of the cell line YB2/3.0.Ag.20 with immunocyte cells sensitized to an immunogen and culturing the hybrid in an in vitro or in vivo culture medium therefor to produce antibodies against the sensitizing immunogen.

23. A process according to claim 22 in which cells of the hybrid myeloma cell line are cultured by inoculating a rat with the hybrid to thereby produce a solid or ascitic tumour, and thereafter isolating the antibodies from the serum and/or ascitic fluid of the rat.

* * * * *